United States Patent [19]
Lanquetin et al.

[11] Patent Number: 5,565,443
[45] Date of Patent: Oct. 15, 1996

[54] SUBCUTANEOUS IMPLANTS BASED ON NORMEGESTROL DERIVATIVES

[75] Inventors: Michel Lanquetin, La Trinite; Jean-Louis Thomas, Charentron-le-Pont; Jacques Paris, Nice, all of France; Elsimar Coutinho, Salvador Bahia, Brazil

[73] Assignee: Laboratoire Theramex S.A., Monaco

[21] Appl. No.: 244,098

[22] PCT Filed: Sep. 17, 1993

[86] PCT No.: PCT/FR93/00900

§ 371 Date: Jul. 6, 1994

§ 102(e) Date: May 17, 1994

[87] PCT Pub. No.: WO94/06437

PCT Pub. Date: Mar. 31, 1994

[30] Foreign Application Priority Data

Sep. 21, 1992 [FR] France .................................. 92 11422

[51] Int. Cl.$^6$ .............................................. A61K 31/56
[52] U.S. Cl. .......................... 514/169; 514/170; 514/177; 514/178; 514/179; 514/182; 424/422; 424/423; 424/424; 424/425; 424/426; 424/484; 424/485; 424/486; 424/487; 424/488

[58] Field of Search ..................... 514/169, 170, 514/177, 178, 179, 182; 424/422, 423, 424, 425, 426, 484, 485, 486, 487, 488

[56] References Cited

U.S. PATENT DOCUMENTS

| | | | |
|---|---|---|---|
| 4,147,783 | 4/1979 | van der Vies | 424/243 |
| 4,172,132 | 10/1979 | Draper et al. | 424/243 |
| 4,456,601 | 6/1984 | Toth et al. | 424/241 |
| 4,544,555 | 10/1985 | Gastaud | 260/397.4 |
| 5,223,492 | 6/1993 | Nasraoui et al. | 514/172 |

OTHER PUBLICATIONS

Nash et al "Steroid Release From Silastic Capsules and Rods" Contraception Oct. 1978, vol. 18, No. 4, pp. 367–394.
Metzker "One Year Contraception with a Single Subdermal Implant Containing Nomegestrol Acetate" Contraception vol. 47, pp. 97–105.

*Primary Examiner*—Nathan M. Nutter
*Attorney, Agent, or Firm*—Bierman and Muserlian

[57] ABSTRACT

Subcutaneous implant for preventing conception for at least one year in women comprising an amount effect to prevent conception without suppressing intermontly bleeding of a steroid compound of formula I or formula II and a physiologically-tolerable pharmaceutical carrier.

12 Claims, 5 Drawing Sheets

SUBCUTANEOUS IMPLANTS BASED ON NORMEGESTROL DERIVATIVES

This invention relates to novel compositions endowed with progestative action and the processes for their production.

It has more particularly as a subject matter novel compositions intended to insure protracted contraception.

Specifically it has as a subject matter, a preparation in the form of a subcutaneous implant containing an effective amount of a derivative of 3-substituted 6-methyl $17\alpha$-$OR_1$ 20-oxo 19-nor pregna 4,6-dien selected from the group consisting of a) 3,20-dioxo 6-methyl $17\alpha$-$OR_1$ 19-nor pregna 4,6-diens of general formula I wherein $R_1$ is a hydrogen, or the acyl moiety of an organic aliphatic, aromatic or cyclanic carboxylic acid having from 2 to 16 carbon atoms b) the substituted 3-$OR_2$ 6-methyl $17\alpha$-$OR_1$ 20-oxo 19-nor pregna 4,6-diens of general formula II wherein $R_1$ has the above-given definitions and $R_2$ is a hydrogen., the acyl moiety of carboxylic acid, or an alkyl radical having from 1 to 8 carbon atoms and c) the 6-methyl $17\alpha$-$OR_1$ 19-nor pregna 4,6-diens of general formula III wherein $R_1$ is defined as above $R_3$ and $R_4$ together form either an oximido grouping of formula =N—O—$R_5$ wherein $R_5$ is a hydrogen, a lower alkyl or a carboxyalkyl group or an alkylenedioxy grouping which may be substituted or each are a lower alkoxy radical in admixture or conjunction with a carrier and with a biologically acceptable diluent.

The implants according to this inventions are made of polymeric materials (hydrophobic, hydrophilic or biodegradable) used as vectors of pharmacologically-active compounds previously included in the formulae I, II or III.

The implants namely are of the container type or of the matrix type.

Among the implants which utilize hydrophobic materials it may be cited:

the implants of container type prepared from polydimethyl siloxanes such as for example SILASTIC® (medical grade of dimethylpolysiloxane made by Dow Corning) produced by the company Dow Corning. This kind of implant is shown in the form of a tube having an external diameter comprised between 2 and 4 mm and having a thickness of about 0.4 mm. The portions of tubing are cut at the selected lengths as a function of the amount of nor pregnadienic compound which is desirably incorporated. The ends of these portions of tube are closed using a glue of medical quality also sold by the company Dow Corning and which belongs to the group of silicones RTV (Room Temperature Vulcanizing).

The amount of nor pregnadienic compound of formulae I, II or III incorporated in the portion of the tube, ranges from 30 to 80 mg and preferably from 45 to 65 mg. This content of active ingredient is namely determined by the granulometric properties of the active ingredient which may be micronized or microcristallized and by its physico-chemical characteristics (molecular weight, solubility, diffusibility, partition index). The way of incorporation of the active ingredient may be done either in the solid state or dispersed in a biologically acceptable and inert carrier.

The manner of preparation and isolation of the microcrystallized forms of the compounds of this invention have already been described in the french patent application 2.668.945 in the name of the applicant.

implants of the container type produced from ethylene/ vinyl acetate copolymers such as for example the material sold under the Trade Name ELVAX® MD 40 (ethylene-vinyl acetate copolymer) by the company DUPONT de NEMOURS. This kind of implant has already been utilized for the intra uterine device Progestasert® containing an hormonal preparation made by Alza, but contrarily to Progestasert in the case of the implants of this invention, the active ingredient is introduced in a solid form.

implants of the matrix type, produced from polydimethyl siloxanes. This kind of implant has already been used in man (Nash, Robertson and cowork—Contraception 18 (1978) p.367). This implant of the matrix type namely presents the inconvenient of a high rate of release of the active ingredient. In order to compensate this disadvantage, the implants according to this invention have to be produced in introducing one of the derivatives according to the formulae I, II or III suspended in a hydrophilic liquid in which the active ingredient is insoluble. This suspension is admixed to the poly dimethyl siloxanes then the whole mass is cross-linked before to proceed to the extrusion of the elastomer in the form of a cylindrical thread having the choosen measures. This process allows the obtention of kinetics of release of zero order and no longer as a function of the square root of time such as the matrix cited by Nash and co-workers.

implants of the matrix type produced from ethylene-vinyl acetate copolymers. In this case the implant is prepared by casting. Due to its monolithic structure, this implant releases the active ingredient along a kinetic of the type square root of the time. The partial coating using a membran which serves to control the release from the matrix, may be realized either with an EVA polymer having a lower concentration of vinyl acetate or in introducing the matrix in a tube of polydimethyl siloxane (type SILASTIC) to obtain release curves of zero order.

Among the implants using hydrophilic materials it may be cited:

implants of matrix type produced from hydroxyethyl polymethacrylates such as for example HYDRON® (a gel based on hydroxyethyl polymethacrylate) manufactured by the company HYDRON HED SCIENCES. This kind of implant is produced by polymeration in alcohol followed by a cross-linking by means of ethylene glycol dimethylacrylate. After desolvatation in a mold, it is obtained in the dry form (vitreous) an implant, the kinetics of which is close to zero order. The process of manufacturing is somewhat inspired from that described by GHIEN Y. W for Norgestomet (J. Pharm. Sci. 65 (1976) 488).

Among the implants using biodegradable materials, it may be cited:

implants of the container type prepared from polycapcolactones manufactured following the process disclosed by PITT and Cowork (J. Pharm. Sci. 68 (1979) 1534). These cylindrical implants obtained by extruding, contain between 30 and 50 mg of one of the nor pregnadienic derivatives of formulae I, II or III suspended in an inert solvent. They have a diameter of 2,4 mm.

implants of matrix type, produced from a polylactic-polyglycolic acid system 50/50 having a molecular weight in the order of 180.000. This kind of implant includes from 20 to 40% of a norpregnadienic derivative of formula I, II or III. It is prepared in dissolving the biodegradable system in methylene chloride to which the active ingredient is added, then in evaporating the solvent. The implant according to the invention is put in the right place using a very large needle after local anesthaesia in the subcutaneous tissue of the region of the buttocks or in the forearm in the women. At the end of the treatment or at any time the implant may be cleared out using a limited surgical intervention under light local anaesthesia.

Among the pharmacologically-active compounds which it is possible to insert in the implants according to this invention, it may be cited:

3,20-dioxo 6-methyl 17α-hydroxy 19-nor pregna 4,6-dien 3,20-dioxo 6-methyl 17α-acetoxy 19-nor pregna 4,6-dien 3-hydroxy 6-methyl 17α-acetoxy 20-oxo 19-nor pregna 4,6-dien 3,17α-diacetoxy 6-methyl 20-oxo 19-nor pregna 4,6-dien 3-pivaloyloxy 6-methyl 17α-acetoxy 20-oxo 19-nor pregna 4-6-dien 3,3-ethylenedioxy 6-methyl 17α-acetoxy 20-oxo 19-nor pregna 4,6-dien 3-methoxyimino 6-methyl 17α-acetoxy 20-oxo 19-nor pregna 4,6-dien 3-carboxymethoxyimino 6-methyl 17α-acetoxy 20-oxo 19-nor pregna 4,6-dien 3,3-[1,2-(R)(R) diethoxycarbonyl ethylene dioxy] 6-methyl 17α-acetoxy 20-oxo 19-nor pregna 4,6-dien The biologically-compatible diluents are pharmacologically-inert powders or vehicles, which are progressively degraded by the biological medium and which serve to dilute, to divide or to distribute the active ingredient—Examples of diluents or vehicles are lactose, mannitol, urea, olive oil or peanut oil.

Since about twenty years, a large number of studies have been performed the wold over place to ascertain an efficient and long lasting way of contraception. The tests performed with very important injectible suspensions of progestatives (Provera® a progestative agent containing 6-methyl-17α-acetoxy-$\Delta^4$-pregnene-3,20-dione . . . ) the duration of which extend over about 6 months, frequently joined with significant side-effects.

This is the reason why the experimenters have been coming to the implants in biocompatible polymers which are inserted either in the uterine cavity (PROGESTASERT(R)) or in the subcutaneous tissues (implants).

It thus has been experienced implants containing numerous steroidal active ingredients with progestational activity, such as norgestrienone, norethindrone or levonorgestrol.

However with these products, it is necessary for obtaining a significantly lenghth of duration, to incorporate a large amount of active ingredient in the implant or better to insert several implants.

Thus Norplant® (a subcutaneous implant of norgestrol sold by American Home Products) which contains as active ingredient Norgestrel has a mean duration of activity of five years for a set of 6 implants of Silastic®. Each implant is filled with 36 mg of crystallized norgestrel, which makes a whole charge of 216 mg of active ingredient.

In contrast thereof the compositions according to this invention request the insertion of only one implant measuring from 30 to 45 mm according to the kind of implant which has been choosen. This way of implantation is significantly simplified and the implant is more easily accepted. The utilization as active ingredient of a norpregnadienic derivative having the general formulae I, II or III as defined as previously, allows an efficient contraception, burdened with minimal side-effects. This utilization insure the persistance of periodical bleedings similar to menses.

More precisely several clinical trials have demonstrated that an implant of the container type based on Silastic® as previously described, containing as active ingredient, nomegestrol acetate, exhibits a contraceptive activity for a period of at least 12 months.

A period of 12 months moreover allows a better monitoring of the subjects.

The following examples are intended to illustrate the invention without limiting it.

EXAMPLE I

Preparation of the Implants of the Container Type Based on Silastic® and Clinical Results The used material is a tube of dimethyl polysiloxane manufactured by the company Dow Corning type 602-265 (catalog reference)

Portions of this tube have been cut at the choosen dimensions. An end of this portion is sealed by an adhesive material suuch as Silastic® type A or type RTV, of medical quality.

The portions are filled with the selected amount of nomegestrol acetate having a controlled granulometric quality. The portions are then closed with the adhesive material. The thus realized implants are thereafter sterilized.

The choice of a definitive size for this implant made of Silastic® has been obtained following preliminary studies performed on volunteers with implants according to example I, of various sizes (20, 30 or 40 mm).

with those of 20 mm lenghth, it occured two pregnancies with those of 30 mm, pregnancies also occured with those of 40 mm it did not appear any conception but the percentage of amenorrhea was high.

The choice has thus been given to an implant of 35 mm lenghth of filling, containing 50±5 mg of nomegestrol acetate.

This implant has been the subject matter of a study performed on 100 women i.e 1085 months/women. The implants have been inserted by subcutaneous way, after local anaesthesia using a 2% procaine solution, in the buttocks area. The subjects were women with genital activity, young (86% were less than thirty years old), in the course of ovarian activity with steady cycles.

80 subjects still take place in this study after one year. 11 subjects have made the implant expelled between 6 and 11 months and only 9 subjects before 6 months.

The reasons for this withdrawal were:
9 cases: preference for another method
3 cases: occurance of menstrual unpunctualities
2 cases: weight taking
3 cases: desire of a pregnancy
3 cases: side-effects (vertigos, dysmenorrheas, head aches).

On a total of 1085 months/women, only one pregnancy occured providing a Pearl's Index of 1.1%.

Bleeding similar to menses occured in all the women but along a rythm which varies from one to another. Out the 80 women which have had one year of implantation, the mean number of bleeding periods is about 12.24±0.29 with a mean duration (in days) of 5.24±0.11. Table I gathers the characteristics of this action in the treated women.

FIG. 1 gathers the menstrual abnormalities (amenorrheas, metrorrhagias, spottings) in the first twenty women which have reached one year of implantation.

An amenorrhea occured in 19 out 100 women on the first month, then the occurance decreases with the time (4.7% on the 11st month). The frequency of the intermonthly bleedings also decreased with the time (from 11% the first cycle to 1% on the last month of utilization).

TABLE I

IMPLANT CONTAINING NOMEGESTROL ACETATE
menstrual scheme over a twelve months treatment
(N = 80 women)

| Parameters | Mean | S.D |
| --- | --- | --- |
| Number of episods of bleeding (+) | 12.24 | 0.29 |
| Mean duration of the bleedings (days) | 5.24 | 0.11 |
| Total number of the days of bleeding | 64.19 | 2.75 |
| Total number of the days of spotting | 7.24 | 1.50 |

TABLE I-continued

IMPLANT CONTAINING NOMEGESTROL ACETATE
menstrual scheme over a twelve months treatment
(N = 80 women)

| Parameters | Mean | S.D |
| --- | --- | --- |
| Total number of the days of bleeding and spotting | 71.42 | 3.22 |
| Mean duration between two consecutive bleeding periods (++) | 24.51 | 0.60 |
| Mean duration of the cycles in days (+++) | 29.80 | 0.60 |
| Longest episod of bleeding (in days) | 10.70 | 0.92 |
| Longest interval without bleeding (in days) | 57.86 | 4.13 |

Figure 1A:
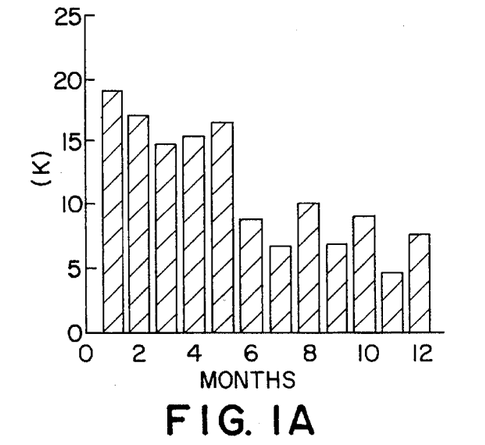
FIG. 1A is a graph of menstrual abnormalities of the data of Example I.
Figure 1B:
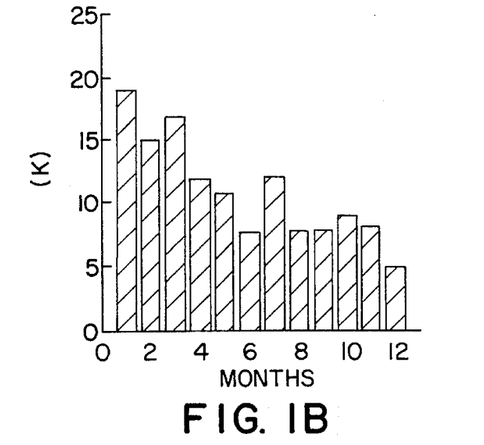
FIG. 1B is a graph of body weight variation and of arterial pressure of Example I.
Figure 1C:
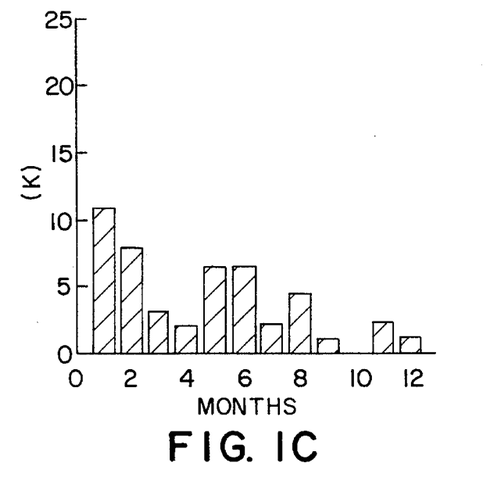
FIGS. 1C and 1D are graphs of intermenstrual bleeding and spotting, respectively on a monthly basis.
Figure 1D:
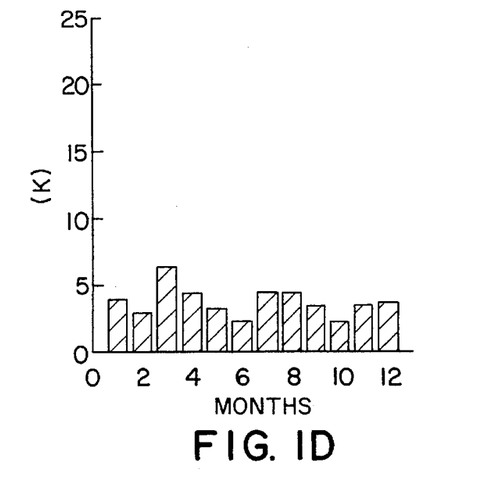
Figure 2A:
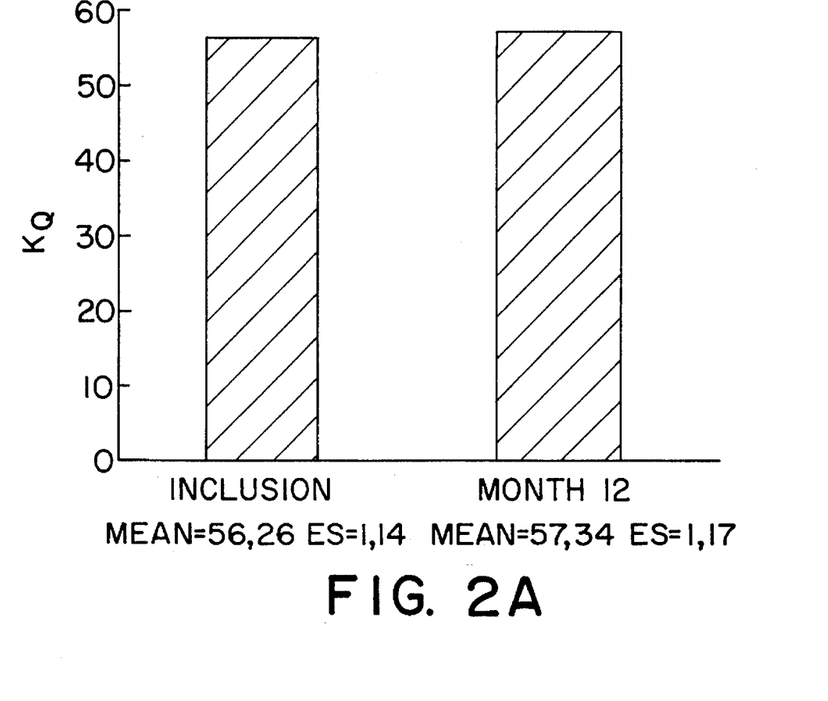
FIGS. 2A and 2B are graphs of the body weight and arterial pressure using Nomegestrol acetate implants, respectively.
Figure 2B:
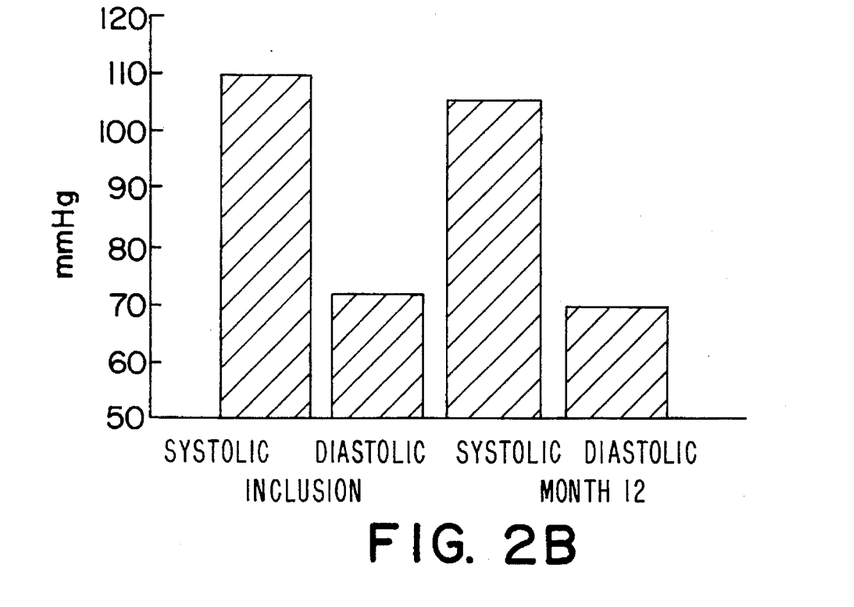
Figure 3:
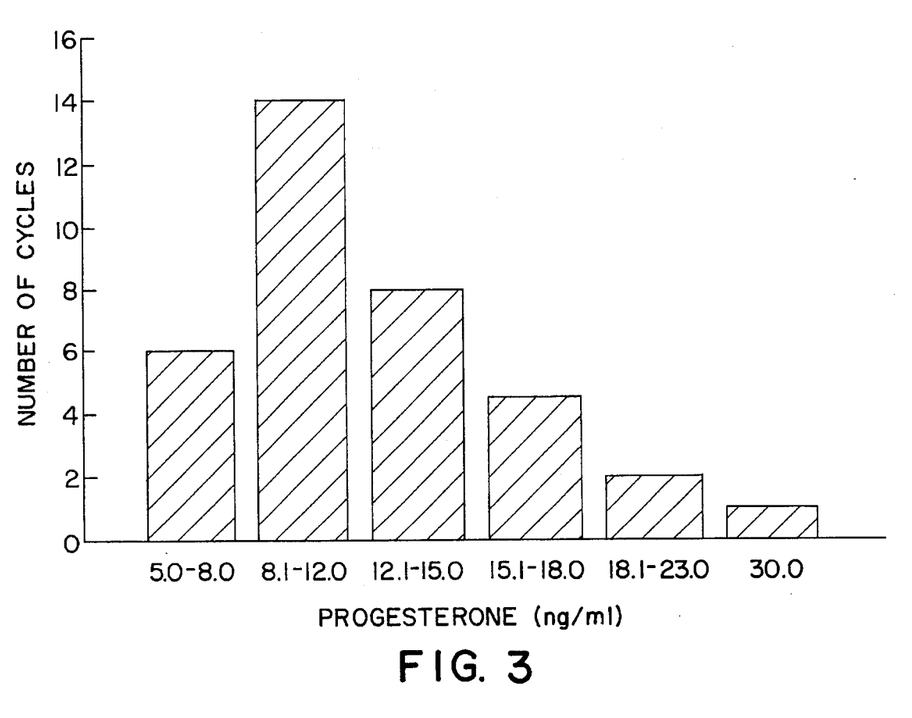
FIG. 3 is a graph of the cycles as a dose of progesterone.

(+) an episod of bleeding is shown with one or several consecutive days of bleeding (with the exception of spotting)
(++) an inverval without bleeding is the interval between two episods of bleeding
(+++) a cycle includes an episod of bleeding and an interval without bleeding FIG. 2. shows the variation of body weight (n=77) and of arterial pressure (n=79) in the women which have beared the implant for one year. It appears a statistically-significative decrease of the systolic pressure (p=0.02). The body weight increased in average of 1.1 kg in a significative manner (p=0.05).

Hormones determination have been carried out in the women having an implant.

a) punctual determinations of progesterone in the second moiety of the "cycle" in twelve subjects and sixty cycles, have first been carried out.

In thirty six cycles, the progesterone level higher to 3 ng/ml testifies the occurance of an ovulation. These values are indicated in table 3.

b) In five women, at least weekly samplings for estradiol and progesterone determinations, have been carried out during the control cycle, for the five or six first cycles of treatment then for the eleventh and twelfth cycles.

Before implantation of the said implant, the cycles were always ovulatory with a level of progesterone of 8.1±4.2 ng/ml and 10.1±3.5 ng/ml respectively at the 18th and at the 24th day of the cycle. Under treatment with an implant of nomegestrol acetate, the levels of progesterone have been lowered but the difference in comparison with the inclusion levels, did become significative only from the 24th day of the second cycle (p<0.05).

In the whole, the lowest levels have been reached in the course of the four first cycles of treatment. At the twelfth cycle of treatment the mean values have been normal, respectively 7.1±1.1 and 15.6±4.7 ng/ml at the 18th and at the 24th day.

As a whole during the studied thirty eight cycles under study only one ovulation (progesterone level higher or equal to 5 ng/ml) has been evidenced out of 24 cases (64.2%).

In the course of the first cycles of treatment of each of the five patients, the progesterone levels have always been lower than 5 ng/ml. In the course of the 12th cycle, the plasmatic levels of progesterone were always compatible with the occurance of an ovulation.

Conclusively, the implant of 35 mm lenghth containing 48 mg nomegestrol acetate is an efficient contraceptive agent for a period of time of at least twelve months, without causing amenorrheas, which have been known to be heavily accepted by the women.

The tolerancy as well as gynaecologic as general, has been good.

EXAMPLE II

Implants of Nomegestrol Acetate of a Matrix Type

It had been prepared a whole mass which forms the elastomer from 70 to 75% of a polyorgano siloxane derivative having silanol end groupings and 24 to 29% silica containing from 0.2 to 0.5% of a selected catalyst.

On the other part, it has been prepared a mixture containing 50% of one of the active ingredients having the formulae I, II or III suspended in an hydrophilic solvent and the whole is intimely admixed in 50% of a polydiorgano-siloxane.

The mixture containing the active ingredient has been incorporated in the composition which forms the elastomer, according to the classical methods known in this art.

The whole mixture is loaded in an extruder to obtain a continuous extrudate, having a diameter of between 2 and 3 mm, depending on the type of implant.

This extrudate is cross-linked by passing it in a ventilated oven at a temperature comprised between 30° and 80° C.

This extrudate is then cutted at the selected dimensions in order to obtain implants of tubular appearance containing from 30 to 60 mg of active ingredient.

For the "in vitro" tests, they have been used implants of an approximative weight of 120 mg containing 25% of active ingredient.

EXAMPLE III

Study on the "In Vitro" Release of Nomegestrol Acetate (3,20-Dioxo 6-Methyl 17α-Acetoxy 19-Nor Pregna 4,6-Dien) in Several Implants It has been performed a comparison of the speed of release of the active ingredient which has been incorporated in three different implants of the matrix type and in one implant of the container type.

These implants have been put in containers containing a known amount of water which has previously been filtered and degased. This medium is changed every 24 hours and the tests lasted over 4 days.

Nomegestrol acetate, released in this medium, has been determined by UV spectrophotometry at 296 nm. For each formulation the determination has been repeated three times. The result are expressed in the form of an average of three determinations and in μg of active ingredient relased per 24 hours. These result are gathered in Tables II and III.

Two out three implants of the matrix type have shown a very similar release profile with a release of 110 μg/day at the steedy state. At the end of 14 days about 14% of the active ingredient have been released.

The release of the active ingredient in the implant of the container type, has been twice lower. In every cases however the kinetics were parallel.

The third implant of the matrix type supplied with a profile of release somewhat different with a more important immediate release.

EXAMPLE IV

Preparation of Implants of the Matrix Type Based on Copolymer Ethylene/Vinyl Acetate (EVA). Results of the Release Study "In Vitro" of Nomegestrol Acetate The implants were prepared by grinding and washing EVA then drying, and mixing with nomegestrol acetate in the proportions of 165 mg EVA for 55 mg active ingredient (i.e 3 parts of EVA for one part of nomegestrol acetate). The mixture being homogeneous is casted, extruded and compressed at temperatures comprised between 50° and 65° C. to produce a cylindrical extrudate of 2.3 mm diameter.

That extrudate is cut every 40 mm to obtain an implant at the desired lenghth. This one has a weight close to 220 mg±10 mg and contains 55 mg nomegestrol acetate (±5 mg).

This matrix is ready to be coated with a porous membran in order that the rate of release will be controlled (PDMS which is polydimethyl siloxane or EVA).

Study of the Matrix Release

Each implant is placed in a 20 ml container having an amount of desionized water (for 24 hours).

This medium is replaced every 24 hours and the experience extends depending on the tests, from 15 to 31 days. The content of nomegestrol acetate in the medium is spectrophotometrically determined at 296 nm.

Figure 4:
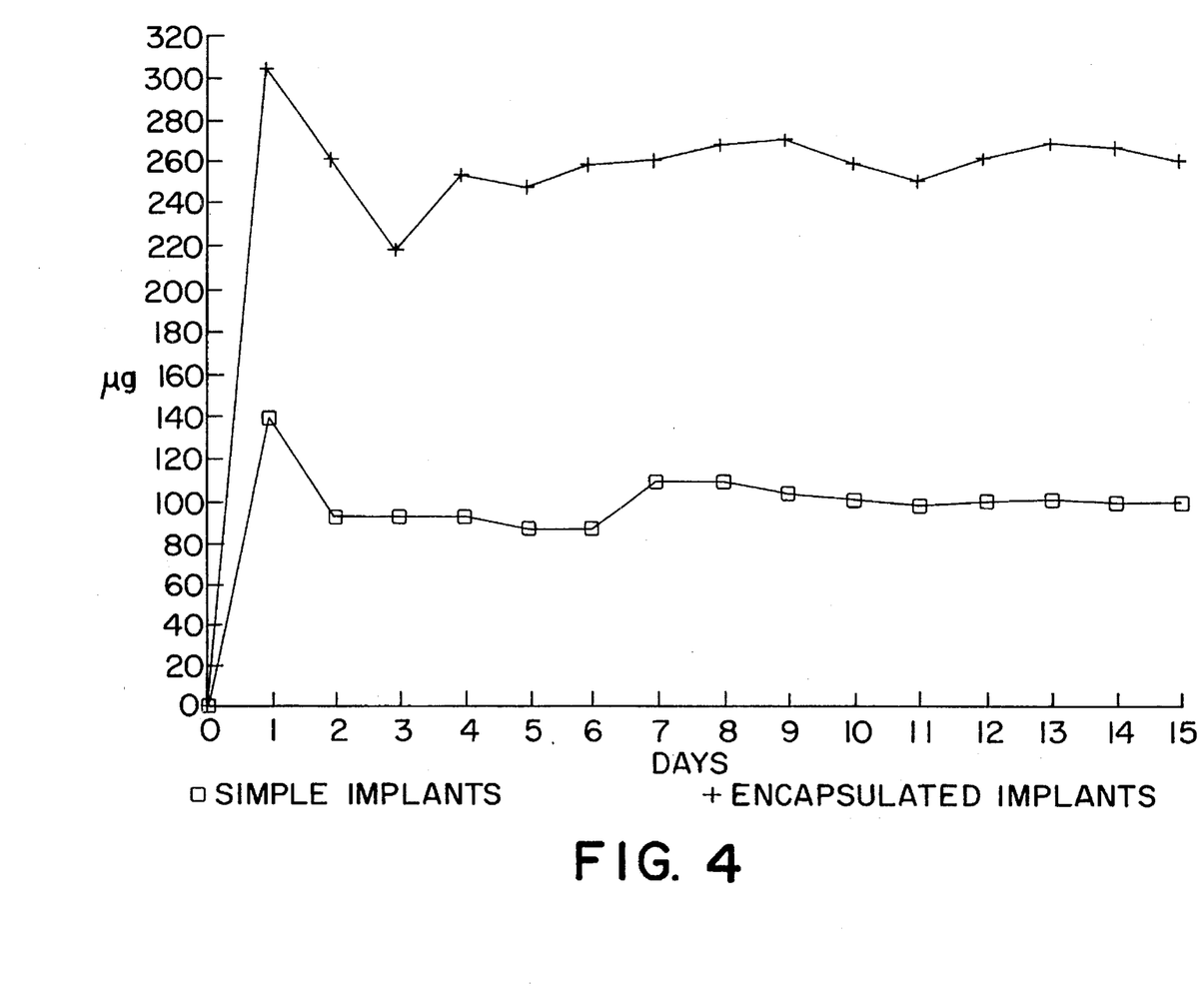
FIG. 4 is a graph of dissolution tests with simple implants and nomegestulated implants.

The results are expressed in μg of active ingredient released per 24 hours. These results are gathered in the FIG. 4 in comparison with an implant based on EVA-copolymer. They show the regularity of the release of the active ingredient after encapsulation with a porous membran and at the same time, the lower release of nomegestrol acetate as a function of the time.

EXAMPLE V

Preparation of the Implants of Matrix Type Based on Vinyl Acetate/Ethylene Copolymer Placed Under a Tubing of Polydimethyl Siloxane The matrix is prepared according to example II and introduced in a tubing of polydimethylsiloxane Medical Grade (Silastic) closed on the two ends with the Silastic sterile glue, type A, Medical Adhesive silicone.

The finished implant is of 3 mm diameter and consists in a cylindrical shape matrix of vinyl acetate/ethylene copolymer having about 2,3 mm diameter and 40 mm lenghth.

The total lenghth is 42 mm after closing with the glue at both ends.

Release Study

It is achieved according to the operational process and the dosage method described at example III.

Figure 5:
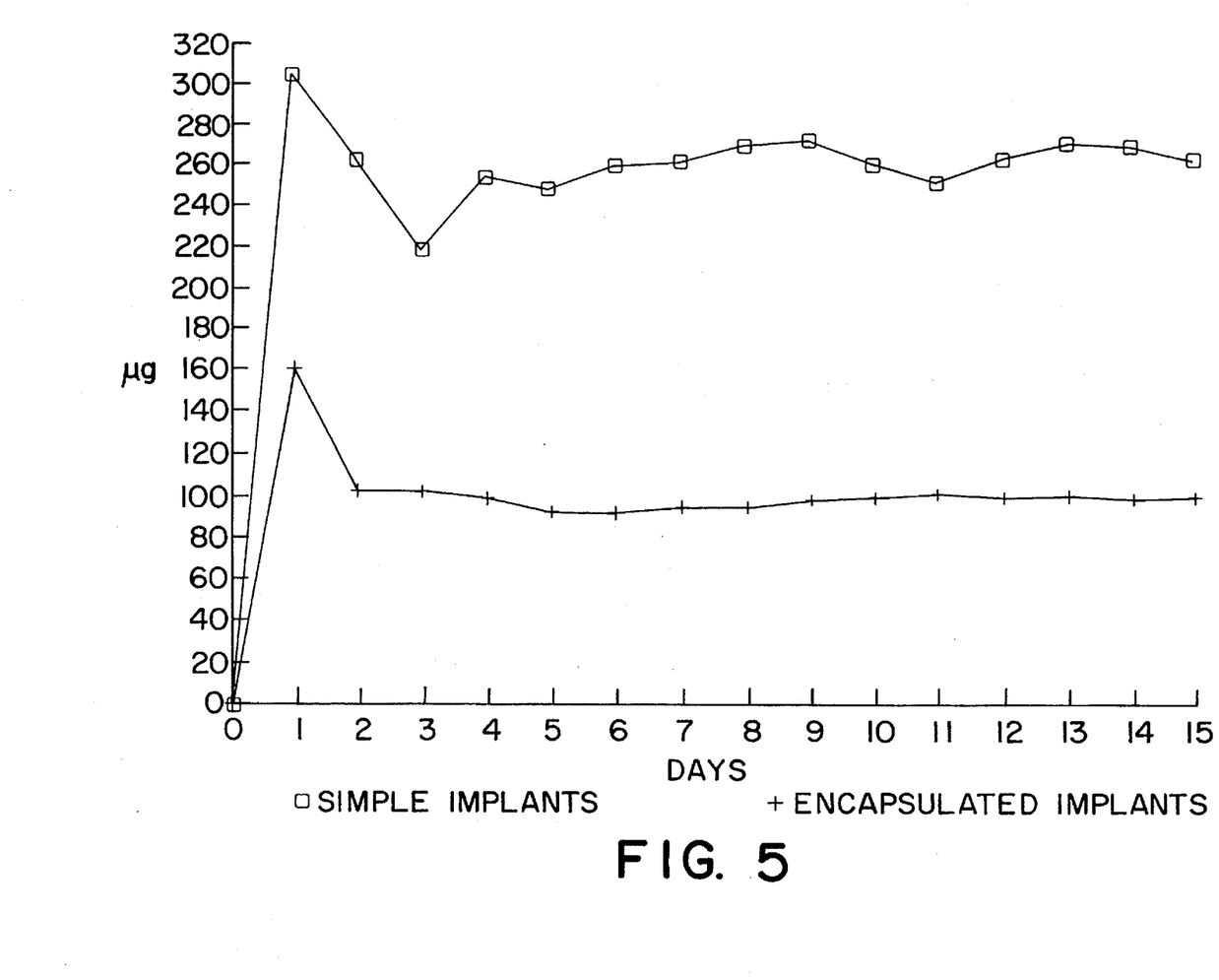
FIG. 5 is a graph showing the μm of Normegestrol acetate released per 24 hours for simple implants and encapsulated implants.

The results are expressed in μg of Nomegestrol acetate released per 24 hours. These results are shown on FIG. 5 in comparison with those obtained in a matrix based on EVA only.

TABLE II

RELEASE OF NOMEGESTROL ACETATE (in μg/day)
FROM THE MATRIX TYPE IMPLANTS
(F 7571-113-11:F 7571-113-13:F 7571-113-15)
and from container type (THERAMEX's implant)
according to this invention

| DAY | F7571-113-11 | F7571-113-13 | F7571-113-15 | THERAMEX's Implant |
|---|---|---|---|---|
| 1 | 184.4 | 210.2 | 186.0 | 103.4 |
| 2 | 142.9 | 206.7 | 146.1 | 71.4 |
| 3 | 128.4 | 209.2 | 132.0 | 65.5 |
| 7 | 492.6 | 663.7 | 490.0 | 201.5 |
| 8 | 111.9 | 189.2 | 116.5 | 54.4 |

TABLE II-continued

RELEASE OF NOMEGESTROL ACETATE (in μg/day)
FROM THE MATRIX TYPE IMPLANTS
(F 7571-113-11:F 7571-113-13:F 7571-113-15)
and from container type (THERAMEX's implant)
according to this invention

| DAY | F7571-113-11 | F7571-113-13 | F7571-113-15 | THERAMEX's Implant |
|---|---|---|---|---|
| 9 | 113.7 | 187.5 | 114.2 | 55.5 |
| 10 | 113.0 | 181.8 | 113.9 | 54.5 |
| 13 | 325.8 | 444.0 | 344.4 | 143.0 |
| 14 | 107.9 | 130.5 | 109.4 | 50.1 |

TABLE III

CUMULATED RELEASE (in μg) OF NOMEGESTROL
ACETATE FROM THE MATRIX TYPE IMPLANTS
(F 7571-113-11:F 7571-113-13:F 7571-113-15)
and from container type implants (THERAMEX's implants)
according to this invention

| DAY | F7571-113-11 | F7571-113-13 | F7571-113-15 | THERAMEX's IMPLANT |
|---|---|---|---|---|
| 1 | 184.4 | 210.2 | 186.0 | 103.4 |
| 2 | 327.3 | 416.9 | 332.1 | 174.8 |
| 3 | 455.7 | 626.1 | 464.1 | 240.3 |
| 7 | 948.3 | 2389.8 | 954.1 | 441.8 |
| 8 | 1060.2 | 1479.0 | 1070.6 | 496.2 |
| 9 | 1173.9 | 1666.5 | 1184.8 | 551.7 |
| 10 | 1286.9 | 1848.3 | 1298.7 | 606.2 |
| 13 | 1612.7 | 2292.3 | 1643.1 | 749.2 |
| 15 | 1720.6 | 2422.8 | 1752.5 | 799.3 |

What is claimed is:

1. A subcutaneous implant for preventing conception for at least one year in women comprising an amount effective to prevent conception without suppressing intermonthly bleeding of a compound having a formula selected from the group consisting of

I

II

III wherein $R_1$ is selected from the group consisting of hydrogen and acyl of an organic carboxylic acid of 2 to 16 carbon atoms, $R_2$ is selected from the group consisting of hydrogen, alkyl of 1 to 8 carbon atoms and acyl of an organic carboxylic acid of 2 to 16 carbon atoms, $R_3$ and $R_4$ are individually alkoxy of 1 to 6 carbon atoms or $R_3$ and $R_4$ together form an alkylenedioxy or $=N-OR_5$ and $R_5$ is selected from the group consisting of hydrogen, alkyl of 1 to 6 carbon atoms and carboxyalkyl of 2 to 6 carbon atoms and a physiologically-tolerable pharmaceutical carrier.

2. An implant of claim 1 wherein the carrier is a biocompatible and sterilizable polymer selected from the group consisting of polydimethylsiloxanes and hydroxyethyl polymethacrylates.

3. An implant of claim 1 wherein the active compound is 6-methyl-17α-$OR_1$-19-nor-$\Delta^{4,6}$-pregnadiene-3,20-dione wherein $R_1$ is hydrogen or acyl of an aliphatic carboxylic acid of 2 to 16 carbon atoms.

4. An implant of claim 3 wherein $R_1$ is hydrogen.

5. An implant of claim 1 wherein the active compound is 6-methyl-17α-acetoxy-19-nor-$\Delta^{4,6}$-pregnadiene-3,20-dione.

6. An implant of claim 2 wherein the polymer is polydimethylsiloxane.

7. An implant of claim 3 wherein the implant contains 30 to 80 mg of the active compound.

8. An implant of claim 2 in the form of a closed cyclinder 20 to 50 mm long and 2 to 4 mm in diameter.

9. An implant of claim 8 wherein the cyclinder is made of an ethylene-vinyl acetate copolymer.

10. A method of preventing conception in a woman by implanting an implant of claim 1 in the woman's subcutaneous tissue.

11. The method of claim 10 wherein the active compound is 6-methyl-17α-acetoxy-29-nor-$\Delta^{4,6}$-pregnadiene-3,20-dione.

12. The method of claim 10 wherein the active compound is 6-methyl-29-nor-$\Delta^{4,6}$-pregnadiene-17α-ol-3,20-dione.

* * * * *